United States Patent
Meier et al.

[11] 3,973,979
[45] Aug. 10, 1976

[54] COLOR PHOTOGRAPHIC MATERIALS CONTAINING DIFFUSION FAST PYRAZOLONE COUPLERS

[75] Inventors: Ernst Meier; Hans Glockner, both of Munich; Karl Kuffner, Unterhaching; Immo Boie, Cologne; Karl-Wilhelm Schranz, Odenthal-Hahnenberg, all of Germany

[73] Assignee: AGFA-Gevaert, A.G., Leverkusen, Germany

[22] Filed: May 14, 1974

[21] Appl. No.: 469,785

[30] Foreign Application Priority Data
May 19, 1973 Germany............................ 2325461

[52] U.S. Cl.................................. 96/100; 96/56; 96/56.5; 260/310 R
[51] Int. Cl.$^2$.......................................... G03C 1/40
[58] Field of Search............................ 96/100, 56.5

[56] References Cited
UNITED STATES PATENTS

| | | | |
|---|---|---|---|
| 3,700,454 | 10/1972 | Sakamoto et al. | 96/100 |
| 3,761,274 | 9/1973 | Inoue et al. | 96/100 |
| 3,785,828 | 1/1974 | Iwama et al. | 96/100 |

*Primary Examiner*—J. Travis Brown
*Attorney, Agent, or Firm*—Connolly and Hutz

[57] ABSTRACT

Improved 5-pyrazolone couplers of the following formula

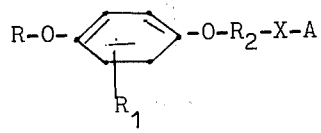

wherein $R, R_1, R_2, X$ and $A$ denotes as described hereinafter for use in lightsensitive color photographic materials which are easy to prepare and give rise after chromogenic development to magenta dyes with improved stability to light.

10 Claims, No Drawings

COLOR PHOTOGRAPHIC MATERIALS CONTAINING DIFFUSION FAST PYRAZOLONE COUPLERS

This invention relates to a color photographic material which contains new diffusion fast pyrazolone couplers for magenta color images which can be used in color photographic materials by chromogenic development.

It is generally known that color images can be produced by a chromogenic development process of photographic silver halide materials which consists of coupling oxidized primary aromatic amine developer compounds with color couplers such as in particular 5-pyrazolones to form dyes. It is also known that magenta couplers based on pyrazolone, in particular, have the disadvantage that the resulting azomethine dye is not sufficiently stable to light so that the dye gradually becomes paler in the course of prolonged exposure to sunlight or UV light. It has already been proposed to improve the stability of dye images against the action of UV radiation by using so-called UV absorbents which are either added to the emulsion layers when they are being developed or, preferably, are added to the emulsion during their preparation. The degree of stability obtained is, however, insufficient, especially in dye images produced from pyrazolone couplers.

It has also been proposed to stabilize dyes against the action of light by means of various additives such as 6-hydroxychroman British patent No. 1,141,817 5-hydroxycoumarin (British patent No. 1,282,706) pyrrogalloldimethylether (German Offenlegungsschrift No. 2,229,059); urea, guanidine or hydroxybenzenes, which are added to the photographic material or to a stabilizing bath. Furthermore, in U.S. Pat. No. 3,519,429, pyrazolone couplers containing phenolic groups have been described which, after chromogenic processing, yield magenta dyes which have increased stability to light. The compounds described in U.S. Pat. No. 3,519,429 however, do not always meet the given requirements because the phenolic group is not sufficiently stable in the chromogenic development process especially when it is exposed to the action of alkaline bath solutions, and it therefore gives rise to undesirable side reactions which may falsify the color of the magenta dye.

The magenta color couplers and the dyes obtained from them by chromogenic development must, in practice, satisfy numerous requirements. The coupling velocity of the color couplers with the oxidation product of the color developer must be sufficiently high. The color couplers and the dyes produced from them must be sufficiently stable at elevated temperatures and against moisture and, as already mentioned above, against light. This applies to both fresh and processed material, for example the residual coupler remaining in the white areas of the image in the processed material must not undergo yellowing. The dyes must also be sufficiently resistant to gaseous reducing or oxidizing agents. They must be fixed in a diffusion-fast form in the image layer and should separate as very fine grain during chromogenic development. Lastly, the dyes obtained from the color couplers by chromogenic development must have a suitable absorption curve with a maximum which corresponds to the color of the desired partial image and with as little side absorption as possible, for example a magenta dye should ideally absorb green light almost completely and be substantially transmittent to red and blue light.

In practice, the introduction of certain chemical groups which improve the properties of the couplers, such as the stabilizing groups described in U.S. Pat. No. 3,519,429 requires considerably more complicated methods of preparation which are in many cases unacceptable on the grounds of cost.

An object of this invention is therefore the preparation of new and improved pyrazolone couplers which have the required properties for use in photographic materials, in particular high lightfastness, and which are also easy to prepare. It now has been found that pyrazolone couplers containing at least one hydroquinone diether group in the 1- or 3-position are eminently suitable for use in light-sensitive color photographic materials, are easy to prepare and give rise, as a result of chromogenic development, to magenta dyes which have improved stability to light.

This invention therefore relates to a light-sensitive color photographic material which contains at least one silver halide layer, which material contains a 5-pyrazolone coupler of the following formula

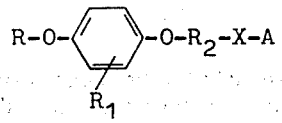

in which
A represents a 5-pyrazolone coupler group which is attached to the connecting member of X in the 1- and/or 3-position of the 5-pyrazolone coupler group either directly or through substituents commonly used in the chemistry of couplers;
X represents a bivalent connecting member, e.g. —O—, —CONH—, —NHCO—, —NHCONH—, —COO— or —OCONH—;
$R_2$ represents an alkylene group preferably containing from 1 to 22 carbon atoms, more preferably containing from 1 to 22 carbon atoms, more preferably a methylene, ethylene, proplyene or butylene group, in which alkylene group one hydrogen atom may be substituted by an alkyl group which preferably contains 1 to 18 carbon atoms, the substituents being preferably in the α-position to the ether oxygen, and, in cases where $R_2$ is attached to the pyrazolone coupler group A through the connecting member —OCONH— the number of carbon atoms in the alkylene group is even;
R represents an alkyl group preferably containing 1 to 18 carbon atoms or a cycloalkyl group, e.g. cyclohexyl or cyclopentyl;
$R_1$ represents hydrogen or an alkyl group preferably containing 1 to 14 carbon atoms, more preferably 4 to 14 carbon atoms.

The particular choice of the pyrazolone coupler group A in formula I according to the invention is not critical. The usual 5-pyrazolone coupler groups which are attached to the group

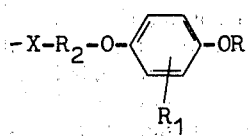

in which X, R, $R_1$ and $R_2$ have the meanings specified above in the 1- or 3-position, either directly or through one or more of the usual substituents found in the chemistry or pyrazolone couplers may be used. The preferred couplers according to the invention are those which, as a result of suitable choice of the substituents in the 1- or 3-position, have the advantageous properties required in practice, e.g. suitable coupling activity and ease of preparation and which give rise in the color development process to dyes which have suitable spectral properties and stability to tropical conditions.

Suitable pyrazolone coupler groups A in the general formula I according to the invention are therefore, in particular, 1-aryl-pyrazolones in which the aryl group in the 1-position to the pyrazolone ring is preferably a benzene ring which may be substituted with substituents, e.g. halogen, alkyl, alkoxy, alkylthio, nitro or alkylsulphonyl. Furthermore, the aryl group in the 1-position to the pyrazolone ring may carry the group

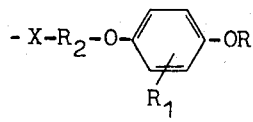

which may be attached either directly or through one of the above mentioned substituents; in the said group, R, $R_1$, $R_2$ and X have the meanings specified above.

Particularly suitable 1-phenyl-pyrazolones-5 according to the invention are those which contain at least one chlorine atom, e.g. in the 2-position of the benzene ring.

Suitable substituents in the 3-position of the pyrazolone coupler group A according to the invention are, for example, alkyl, alkoxy alkylamino, arylamino or acylamino groups or the group

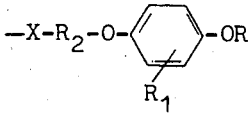

in which R, $R_1$, $R_2$ and X have the meanings defined above. These substituents may, in turn, be substituted with groups which reduce the tendency of the couplers to diffusion or, if desired, they may be substituted with groups which increase the tendency to diffusion, or they may be substituted with groups which improve the spectral properties of the couplers, e.g. halogen, alkyl, alkoxy, alkylthio, nitro, acyl, acyloxy, acylamino, carbamyl or sulfamyl groups or the group

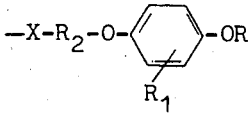

wherein R, $R_1$, $R_2$ and X have the meanings defined above.

The couplers according to the invention are characterized by the fact that dyes obtained from them by development have a greater stability to light compared with dyes from couplers of the known art which do not contain hydroquinone diether groups, e.g. the couplers described in Russian Pat. No. 141,485 or British patent No. 956,261.

The advantageous properties of the pyrazolone couplers are in no way deleteriously effected by introduction of the hydroquinone diether group through the connecting member $R_2$—X defined above.

Attachment of the group

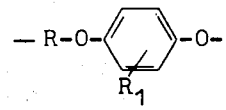

to the pyrazolone group A through the connecting member-$R_2$—X— in which $R_2$ and X have the meanings defined above can be carried out easily and without problems.

The following Table 1 shows examples of suitable hydroquinone diether groups which according to the invention may be connected to the pyrazolone coupler either directly or through one or more substituents, in particular through an aniline or phenyl group in the 1- or 3-position.

TABLE 1

R—O—⟨⟩—O—$R_2$—X—
            $R_1$

| R | $R_2$ | X | $R_1$ |
|---|---|---|---|
| $C_{12}H_{25}$ | $CH_2$ | CONH | H |
| $C_{12}H_{25}$ | $CH_2$ | CONH | t-butyl |
| $CH_3$ | CH($C_{12}H_{25}$) | CONH | H |
| $C_{12}H_{25}$ | CH($C_2H_5$) | CONH | H |
| $C_{14}H_{29}$ | $CH_2$—$CH_2$ | OCONH | H |
| $C_{18}H_{37}$ | $CH_2$—$CH_2$ | OCONH | H |
| $C_{12}H_{25}$ | $CH_2$—$CH_2$ | OCO | H |
| ⟨furyl⟩ | $CH_2$—$CH_2$ | OCONH | $C_8H_{17}$ |
| $CH_3$ | $CH_2$—$CH_2$ | O | $C_{12}H_{25}$ |
| $CH_3$ | $CH_2$—$CH_2$ | O | H |
| $C_{12}H_{25}$ | $CH_2$—$CH_2$ | O | H |
| $C_8H_{17}$ | $CH_2$—$CH_2$ | O | H |
| ⟨pyridyl⟩ | $CH_2$—$CH_2$ | O | t-butyl |
| $C_{12}H_{25}$ | $CH_2$—$CH_2$ | OCONH | H |
| $C_{10}H_{21}$ | $CH_2$—$CH_2$ | OCONH | H |
| $C_8H_{17}$ | $CH_2$—$CH_2$ | OCONH | t-butyl |
| $C_5H_{11}$ | $CH_2$—$CH_2$ | OCONH | t-butyl |
| $C_{12}H_{25}$ | $CH_2$—$CH_2$ | NHCO | H |
| $C_{12}H_{25}$ | $CH_2$—$CH_2$ | NHCONH | H |
| $(CH_3)_2CH$—$CH_2$ | $CH_2$—$CH_2$ | OCO | H |
| $C_{12}H_{25}$ | $CH_2$—$CH_2$—$CH_2$ | O | H |
| $CH_3$ | $CH_2$—$CH_2$—$CH_2$ | CONH | $C_{12}H_{25}$ |
| $C_{12}H_{25}$ | $CH_2$—$CH_2$—$CH_2$ | CONH | H |
| $C_{12}H_{25}$ | $CH_2$—$CH_2$—$CH_2$—$CH_2$ | NHCO | H |
| H | $CH_2$—$CH_2$—$CH_2$—$CH_2$ | NHCO | H |

Pyrazolone couplers according to the invention which are particularly easy to prepare are those in which $R_2$ is a methylene, ethylene, propylene or butylene group, any of which groups may contain an alkyl group containing from 1 to 18 carbon atoms, preferably in the α-position to the ether oxygen, and in which if X is the bivalent connecting member OCONH, the number of carbon atoms in the alkylene chain is even; and, furthermore, if the bivalent connecting member X is —O—, then $R_2$ is an alkylene group containing from 2 to 22 carbon atoms, preferably an ethylene, propylene or butylene group, which alkylene groups may be substituted with alkyl groups containing from 1 to 18 carbon atoms.

The following are examples of suitable couplers according to the invention:

8. 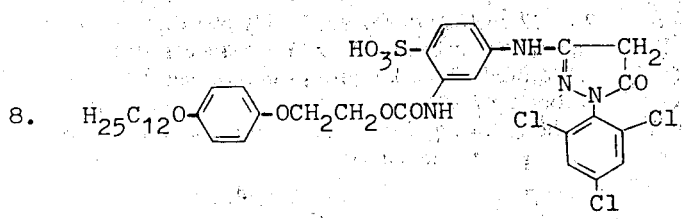
9. 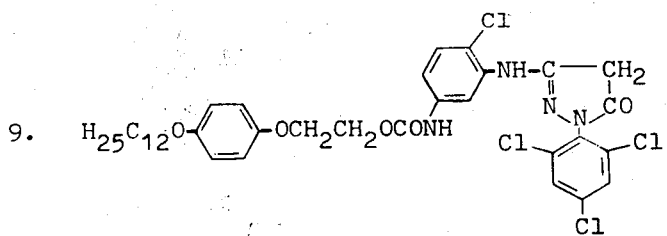
10. 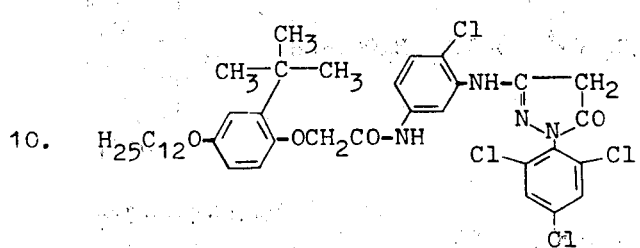
11. 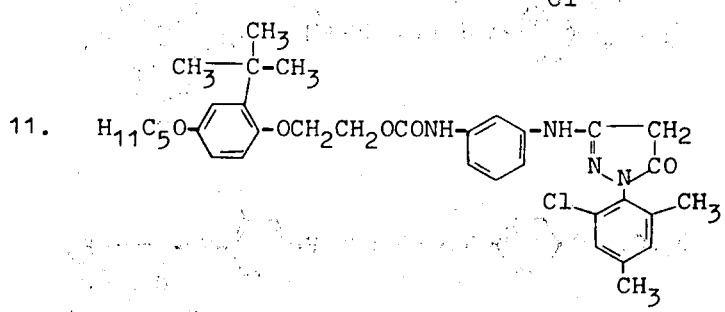
12. 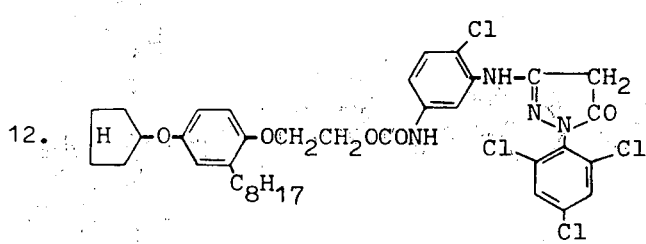
13. 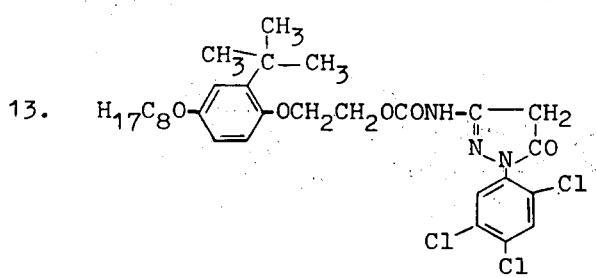
14. 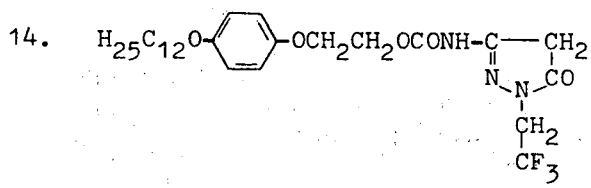

15. $H_{25}C_{12}O-\underset{}{\underset{}{\bigcirc}}-OCH_2CH_2NHCONH-\underset{N}{\overset{}{\underset{\|}{C}}}\underset{\underset{Cl}{\underset{|}{\bigcirc}}-SO_2CH_2Cl}{\overset{CH_2}{\underset{CO}{|}}}$ 16. $H_{25}C_{12}O-\bigcirc-OCH_2CH_2NH-CO-\bigcirc-NH-\underset{N}{\overset{}{C}}\underset{\underset{Cl}{\bigcirc}\underset{Cl}{}}{\overset{CH_2}{\underset{CO}{|}}}$ 17. $H_{25}C_{12}O-\bigcirc-OCH_2CH_2CH_2NHCO-\bigcirc-NH-\underset{N}{C}\underset{\underset{Cl}{\bigcirc}\underset{Cl}{}}{\overset{CH_2}{\underset{CO}{|}}}$ 18. $H_{25}C_{12}O-\bigcirc-OCH_2CH_2NHCO-\underset{}{\bigcirc}-\overset{Cl}{}\underset{}{NH}-\underset{N}{C}\underset{\underset{Cl}{\bigcirc}\underset{OCH_3}{Cl}}{\overset{CH_2}{\underset{CO}{|}}}$ 19. $CH_3O-\underset{\underset{C_{12}H_{25}}{|}}{\bigcirc}-OCH_2-CH_2CH_2-CONH-\underset{N}{C}\underset{\underset{CH_2}{|}\underset{\bigcirc}{}}{\overset{CH_2}{\underset{CO}{|}}}$ 20. $H_{25}C_{12}O-\bigcirc-O\underset{\underset{}{\overset{C_2H_5}{|}}}{CH}-CONH-\underset{N}{C}\underset{\underset{}{\bigcirc}\underset{NO_2}{}}{\overset{CH_2}{\underset{CO}{|}}}$ 21. $H_{25}C_{12}O-\bigcirc-OCH_2CH_2CH_2O-\underset{N}{C}\underset{\underset{Cl}{\underset{Cl}{\bigcirc}}\underset{SO_3H}{Cl}}{\overset{CH_2}{\underset{CO}{|}}}$ 22. $H_{25}C_{12}O-\bigcirc-OCH_2CH_2CH_2O-\underset{N}{C}\underset{\underset{Cl}{\bigcirc}\underset{Cl}{Cl}}{\overset{CH_2}{\underset{CO}{|}}}$

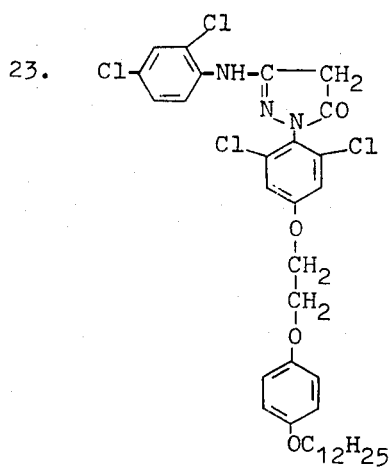

27. 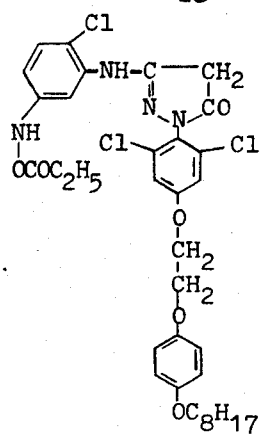
28. 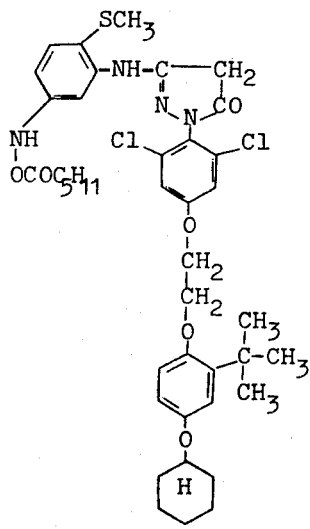
29. 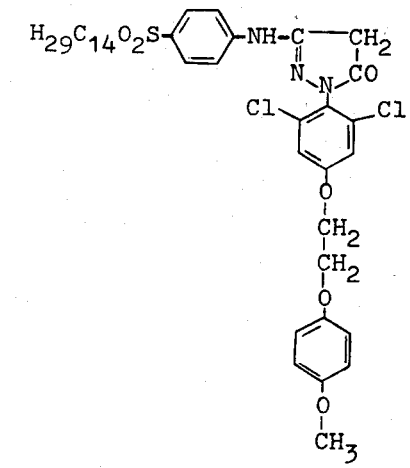
30. 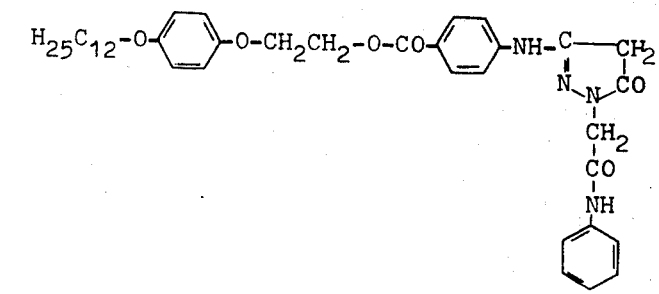

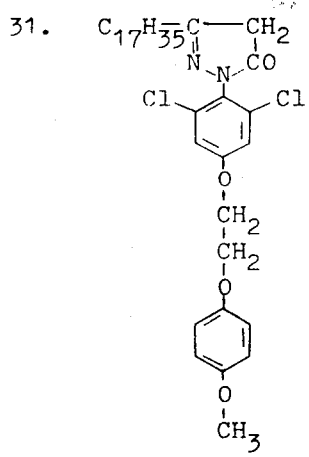
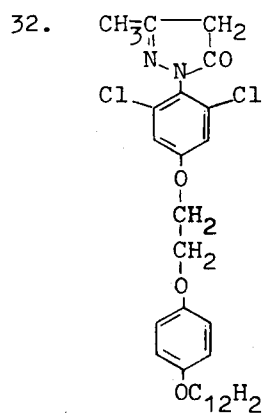

The couplers according to the invention are superior to the couplers described in U.S. Pat. No. 3,519,429.

1. The couplers according to the invention undergo no undesirable side reactions in the color development process and, moreover, are more easily obtainable both because the reaction time is shorter and because the method of preparation involves two stages less, as can be seen from the reaction scheme below.

Preparation of the coupler according to the invention is carried out in four stages as illustrated below by the example of a coupler according to the invention in which $R_2$ denotes —CHR'— and X denotes —CONH—. The group R shown in the following reaction scheme have the same meaning as defined above, R' denotes hydrogen or alkyl and K denotes a pyrazolone coupler group.

1st Stage

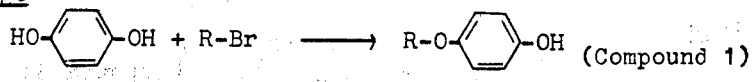 (Compound 1)

2nd Stage

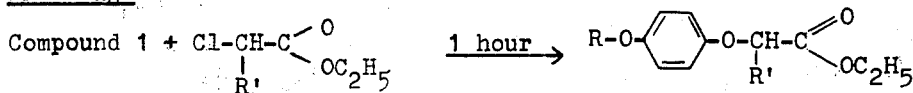 (Compound 2)

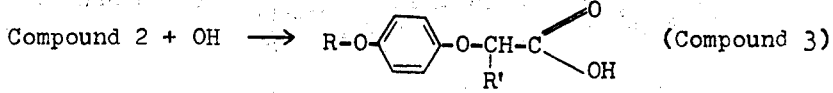 (Compound 3)

3rd Stage

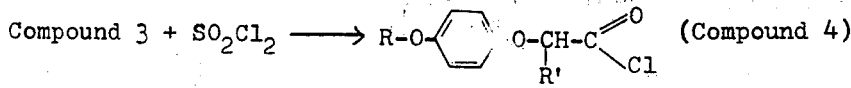 (Compound 4)

4th Stage

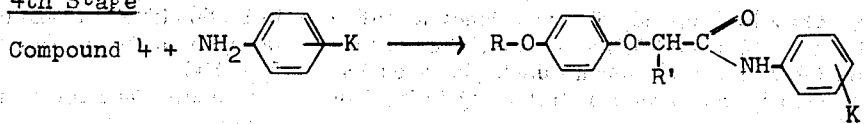

The preparation of the coupler described in German Auslegeschrift No. 1,547,803 which contains a phenolic stabilizer group, however, takes place in 7 stages as shown in the reaction scheme below in which the groups R' and K have the meanings defined above.

1st Stage

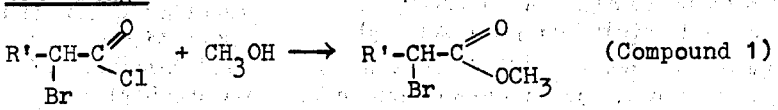 (Compound 1)

2nd Stage

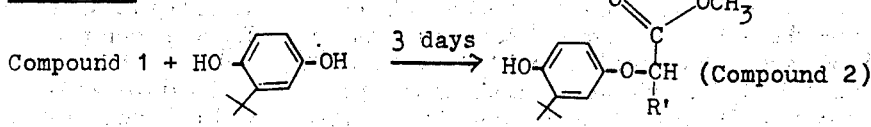 (Compound 2)

3rd Stage

Compound 2 + OH⁻ ⟶ (structure) (Compound 3)

4th Stage

Compound 3 + acetyl chloride ⟶ (structure) (Compound 4)

5th Stage

Compound 4 + SOCl₂ ⟶ (structure) (Compound 5)

6th Stage

Compound 5 + H₂N—⟨⟩—K ⟶ (structure) (Compound 6)

7th Stage

Compound 6 + H⁺ ⟶ (structure)

When preparing the couples according to the invention, the reaction of stage 2 takes about one hour but long reaction times are required for stage 2 to prepare the coupler of the art. Moreover, the intermediate compound 2 for preparing the pyrazolones according to the invention is obtained very pure and can be saponified in the same reaction mixture to yield the intermediate compound 3 without first being isolated or purified.

The color couplers according to the invention can be prepared in high yields by the usual processes known in the art. The stabilizing group is also introduced by known methods in a non-coupling position of the coupler molecule.

The preparation of several couplers according to the invention is described below.

EXAMPLE OF PREPARATION 1 FOR COUPLER NO. 1

1-(2,4,6-Trichlorophenyl)-3-[3-(4-dodecyloxy-phenoxyacetamido)-anilino]pyrazolone (5)

a. Intermediate compound 1: 4-Dodecyloxyphenol 660 g (6mol) of hydroquinone were dissolved in 3 l of absolute ethanol with stirring and mild heating. 224 g (4 mol) of potassium hydroxide were added under an atmosphere of nitrogen and a mixture of 500 g (2 mol) of dodecylbromide and 500 ml of absolute ethanol was added dropwise over a period of 4 hours under reflux. After the reaction mixture had been boiled for one hour more it was poured on to 7 l of water and the resulting oil-water mixture was acidified with glacial acetic acid. The product was left to solidify overnight, suction filtered, washed with water and thoroughly pressed out. The crude product was dissolved in 2 l of hot ethanol while still moist and then cooled to 30°C. The diether compound which crystallized was removed by suction filtration. 4-Dodecyloxyphenol then precipitated on further cooling to 5°C. Yield: 350 g(M.p. 77°–78°C.)

b. Intermediate compound 2: 4-Dodecyloxyphenoxyacetic acid 278 g (1mol) of 4-dodecyloxyphenol and 245 g (2 mol) of ethyl chloroacetate were heated to 90°C. 216 (1.2 mol) of a 30% sodium methylate solution were added dropwise to the melt and the reaction mixture was boiled under reflux for 1 hour. The ethyl ester was saponified by boiling it for 1 hour more with 275 ml of 30% sodium hydroxide solution and 275 ml of methanol. The sodium salt of intermediate compound 2 precipitated from the reaction solution when cold. It was converted into the free acid by recrystallization from glacial acetic acid and a little hydrochloric acid. Yield: (280 g. M.p. 120°C.)

c. Intermediate compound 3: 4-Dodecyloxy-phenoxyacetyl chloride 84 g of 4-Dodecyloxyphenoxyacetic acid were boiled under reflux for 3 hours with 190 ml of thionyl chloride. After removal of excess thionyl chloride by distillation, the acid chloride remained as a dark oil which could be used for the next stage of the reaction without further purification.

d. Coupler No. 1

38 g (0.107 mol) of intermediate compound 3 were added dropwise with stirring to a solution of 38 g (0.1 mol) of 1-(2,4,6-trichlorophenyl)-3-(3-amino-anilino)-pyrazolone-(5) and 8.3 g (0.2 mol) of anhydrous sodium acetate in 250 ml of glacial acetic acid at 25°C under a nitrogen atmosphere. The reaction mixture was stirred into 2 l of water after 1 hour. The resulting precipitate was suction filtered and dried. 33 g of coupler No. 1 M.p. 82°–83°C, were obtained by recrystallizing the precipitate several times from acetonitrile.

EXAMPLE OF PREPARATION 2 FOR COUPLER NO. 2

1-(2,6-Dichloro-4-methoxy-phenyl)-3-(2-chloro-5-[4-dodecyloxyphenoxy-ethyloxy carbonamido]-pyrazolone)-(5)

a. Intermediate compound 1: $\beta$-(4-Dodecyloxyphenoxy)-ethanol 278 g (1 mol) of 4-dodecyloxyphenol (for preparation see compound 1 from Example 1) together with 169 g (2.1 mol) of 2-chloroethanol and 1000 ml of absolute ethanol were heated to 40°C with stirring. 84 g (2.1 mol) of sodium hydroxide were then added and the reaction mixture was stirred for 5 hours at 50° to 60°C. The crude product was precipitated by stirring the reaction mixture into 3 l of water. 300 g of intermediate compound 1, M.p. 82°–83°C, were obtained by recrystallization from 1.5 l of ethanol.

b. Intermediate compound 2: $\beta$-(4-Dodecyloxyphenoxy)-ethyl chloroformate

Phosgene was introduced into 800 ml of carbon tetrachloride at 10° to 15°C with stirring until 110 g (1.1 mol) had been taken up. A mixture of 322 g (1 mol) of intermediate compound 1 and 121 g (1 mol) of N,N-dimethylaniline and 1 l of carbon tetrachloride, which had been dissolved on a water bath, was added dropwise to this solution through a heatable dropping funnel over a period of about 3 hours. When all the mixture had been added, the reaction mixture was heated to 40°C for 1 hour. After it had cooled down to 5°C, 1 l of cold water was added and the mixture was vigorously stirred. When the excess phosgene had been hydrolyzed the reaction solution was washed twice with dilute hydrochloric acid and twice with water. After removal of carbon tetrachloride by distillation, 380 g of intermediate compound 2 was obtained with a degree of purity of 96.5%.

c. Coupler No. 2

4.40 (0.011 mol) of intermediate compound 2 were added to a solution of 4 g (0.01 mol) of 1-(2,6-dichloro-4-methoxyphenyl)-3-(2-chloro-5-amino-anilino)-pyrazolone-(5) and 0.82 g (0.01 mol) of anhydrous sodium acetate in 50 ml of glacial acetic acid at 50°C with stirring and under a nitrogen atmosphere. The reaction mixture was stirred into 500 ml of water after 1 hour. After suction filtration and drying, the crude product was purified by column chromatography (diluent ethyl acetate/hexane 1:3) over silica gel. Yield: 4.8 g M.p. 60°–62°C.

EXAMPLE OF PREPARATION 3 FOR COUPLER No. 8

1-(2,4,6-Trichlorophenyl)-3-(3-[4-dodecyloxyphenoxyethyloxycarbonamido]-4-sulpho-anilino)-pyrazolone-(5)

13.2 g (0.033 mol) of intermediate compound 2 of Example 2 were added at 60°C with stirring to a solution of 13.5 g (0.03 mol) of 1-(2,4,6-trichlorophenyl)-3-(3-amino-4-sulpho-anilino)-pyrazolone-(5) and 7.4 g (0.09 mol) of anhydrous sodium acetate in 180 ml of glacial acetic acid. The reaction mixture obtained after 1 hour's stirring was cooled to 5°C and the precipitate was suction filtered. 12.2 g of coupler 8 were obtained after recrystallization from methanol.

EXAMPLE OF PREPARATION 4 FOR COUPLER NO. 14

1-($\beta,\beta,\beta$-trifluoroethyl)-3-(4-dodecyloxyphenoxy-ethyloxycarbonamido)-pyrazolone-(5)

12 g (0.09 mol) of powdered anhydrous aluminium chloride were carefully introduced into 220 ml of pyridine at room temperature with stirring. The temperature of the reaction solution rose to 50°–60°C. 18.1 g (0.2 mol) of 1-($\beta,\beta,\beta$,-trifluoroethyl)-3-amino-pyrazolone-(5) were then added at this temperature, followed after 5 minutes by 44 g (0.11 mol) of 4-dodecyloxyphenoxy-ethylchloroformate (intermediate compound 2, Example 2). The reaction mixture was stirred into 1 l of 10% hydrochloric acid after 1 hour. The resulting precipitate was suction filtered and washed with 2N hydrochloric acid and water. The dried crude product was recrystallized from ethyl acetate. Yield: 32 g, (M.p. 138°C.)

EXAMPLE OF PREPARATION 5 FOR COUPLER No. 6

1-(2,4,6-Trichlorophenyl)-3-(2-chloro-5-[$\alpha$-(4-methoxyphenoxy)-myristoylamido] anilino)-pyrazolone-(5)

a. Intermediate compound 1: $\alpha$-(4-Methoxyphenoxy)myristic acid 21.6 g (0.12 mol) of 30% sodium methylate solution were added to a mixture of 12.4 g (0.1 mol) of 4-methoxyphenol and 33.5 g (0.1 mol) of $\alpha$-bromomyristic acid ethyl ester at an oil bath temperature of 100°C with stirring and the reaction mixture was boiled under reflux for one hour. A mixture of 27.5 ml of 30% sodium hydroxide solution and 27.5 ml of methanol was then carefully introduced and the whole reaction mixture boiled for one hour more. The alkaline solution was then stirred into 200 ml of water and 30 ml of concentrated hydrochloric acid. The precipitated oil was taken up with chloroform and the solution in chloroform was shaken several times with water and the chloroform was distilled off. 35 g of residue were obtained.

b. Intermediate compound 2:$\alpha$-(4-Methoxyphenoxy)-myristic acid chloride 8.75 g of intermediate compound 1 were boiled with 19 ml of thionyl chloride under reflux for 3 hours. The excess thionyl chloride was distilled off and the residue was processed without purification.

c. Coupler No. 6

Intermediate compound 2 was diluted with 25 ml of glacial acetic acid and added dropwise to a solution of 8.5 g of 1-(2,4,6-trichlorophenyl)-3-(2-chloro-5-amino-anilino)-pyrazolone-(5) and 2.3 g of sodium acetate in 65 ml of glacial acetic acid which was, at the same time, stirred under an atmosphere of nitrogen, The solution was kept at 70°C by heating. The acid chloride was added at room temperature. After one hour, the reaction mixture was stirred into 600 ml of water and the resulting precipitate was suction filtered and dried. The crude product was purified by column chromatography (silica gel, diluent: 3 : 1 mixture of

EXAMPLE OF PREPARATION 6 FOR COUPLER No. 17

1-(2,4,6-Trichlorophenyl)-3-(4-[δ-4-dodecyloxy-phenoxybutylaminocarbonyl]-anilino)-pyrazolone a. Intermediate compound 1:γ-(4-Dodecyloxy-phenoxy)-butyronitrile A hot solution of 278 g (1 mol) of 4-dodecyloxyphenol in 400 ml of absolute ethanol was added to a solution of 23 g (1 mol) of sodium in 650 ml of absolute ethanol, and to this mixture, 124 g (1.2 mol) of γ-chlorobutyronitrile in 170 ml of absolute ethanol were added dropwise over a period of 1 hour with stirring. After 6 hours' boiling under reflux, the precipitated sodium chloride was filtered off while still hot. The nitrile precipitated from the solution when cold. Yield: 212 g (M.p. 67°–68°C.)

b. Intermediate compound 2:δ-(4-Dodecyloxyphenoxy)-butylamine 185 g of intermediate compound 1 were suspended in 3 l of a 10% methanolic ammonia solution and hydrogenated with Raney nickel at 100°–120°C and 100 excess atmospheres of hydrogen in an autoclave. The amine which pecipitated from the solution was recrystallized from ethanol. Yield: 110 g(M.p. 66°–70°C.)

c. Intermediate compound 3: 4-Nitrobenzoyl-δ-(4-dodecyloxy-phenoxy)-butylamide 40.8 g (0.02 mol) of 4-nitrobenzoyl chloride were added dropwise to a solution of 70 g (0.2 mol) of intermediate compound 2in 650 ml of benzene and 35 g (0.45 mol) of pyridine with stirring at 25°C and the mixture was then boiled under reflux for 2 hours. After removal of the benzene by distillation, the residue was triturated with water and suction filtered. 90 g of amide melting at 98°C were obtained after recyrstallization from alcohol.

d. Intermediate compound 4: 4-Aminobenzoyl-δ-(4-dodecyloxy-phenoxy)-butylamide.

90 g of nitro compound (intermediate compound 3) were hydrogenated in 700 ml of ethanol at a hydrogen pressure of 25 excess atmospheres with the aid of Raney nickel at 60°C. The amine crystallized from the solution. Yield: 72 g(M.p. 94°–95°C.)

e. Intermediate compound 5:β-(4δ-[4-dodecyloxy-phenoxylbutylamidocarbonyl]anilino)-β-imino-propionic acid ethyl ester hydrochloride 46.9 g (0.2 mol) of intermediate compound 4 and 26.8 g (0.11 mol) of β-phenoxy-β-imino-propionic acid ethyl ester .HCl (preparation according to British patent application Ser. No. 00456/74 which is described below) in 100 ml of ethyl acetate were stirred for 1 hour at 80°C. When the reaction mixture was cold, 150 ml of petroleum ether were added and the resulting precipitate was suction filtered. Yield 56 g f. Coupler No. 17

32.5 g (0.0525 mol) of intermediate compound 5 were boiled under reflux with 10.6 g (0.05 mol) of 2,4,6-trichlorophenylhydrazine in 80 ml of methanol and 1.5 ml of glacial acetic acid for 4 hours. The product obtained after cooling was suction filtered and stirred together with a solution of 1.2 g of sodium in 60 ml of methanol at room temperature for 90 minutes. Coupler 17 precipitated after acidification with glacial acetic acid. The product was recrystallized from ethyl acetate. Yield 18.5g (M.p. 152°–55°C.)

benzene and ethyl acetate). Yield: 8.9 g(M.p. 68°–70°C.)

EXAMPLE OF PREPARATION 7 FOR COUPLER NO. 22

1-(2,4,6-Trichlorophenyl)-3-(γ-4-dodecyloxyphenoxypropyloxy)-pyrazolone-(5)

a. Intermediate compound 1: 1-(2,4,6-Trichlorophenyl)-3-methoxy-pyrazolone-(5)

28 g of β-Methoxy-β-2,4,6-trichlorophenyl-hydrazinoacrylic acid ethyl ester (for method of preparation see German Offenlegungsschrift No. 2,042,921) were dissolved in 200 ml of methanol and then stirred for 30 minutes after the addition of 9 ml of 30% sodium hydroxide solution. 18g of pyrazolone precipitated after the solution had been acidified with glacial acetic acid. M.p. 166°C.

b. Coupler No. 22

10 g of intermediate compound 1 and 25 g of 3-(4-dodecyloxyphenoxy)-propanol (method of preparation similar to that of intermediate product 1, Example 2, using 3-chloropropanol) were melted in an oil bath at 130°C. 3 ml of 50% sulfuric acid were added to the melt and the mixture was stirred for 3 hours. 5.6 g of the coupler could be isolated from the crude product by column chromotography (silica gel, ethyl acetate/hexane).

EXAMPLE OF PREPARATION 8 FOR COUPLER NO. 24

1-(2,6-Dichloro-4-β-[4-dodecyloxyphenoxy]-ethoxyphenyl)-3-(2-methoxy-5-diethylamido-sulphonyl-anilino)-pyrazolone-(5)

a. Intermediate compound 1: 2,6-Dichloro-4-β-chloroethoxyaniline

A mixture of 200 ml of chloroethanol and 200 ml of benzene was saturated with gaseous hydrogen chloride. 58 grams of p-nitrosophenol were introduced under a nitrogen atmosphere with stirring over a period of 2 hours at 25°–30°C. Towards the end of the addition of nitrosophenol, th mixture was diluted with benzene to keep the resulting paste in a stirrable condition. The hydrochloride was suction filtered and washed with ether. The crude product was dissolved in 300 ml of hot ethanol and poured on to 1 l of water. The free amine obtained in this way was recrystallized from ethanol. Yield: 32g (M.p. 64°–66°C.)

b. Intermediate compound 2: 2,6-Dichloro-4-dodecyloxyphenoxy-ethoxy-aniline 2.3 g(0.1 mol) of sodium were dissolved in 250 ml of methyl glycol. 27.8 g (0.1 mol) of 26.5 g of intermediate compound 1 were added successively to this solution which was then refluxed for 5 hours. The methyl glycol was distilled off and the residue dissolved hot in 500 ml of ethanol. 32 g of the desired product were obtained after cooling to 5°C. M.p. 75°–77°C.

c. Intermediate compound 3: 2,6-Dichloro-4-dodecyloxyphenoxy-ethyloxy-phenyl hydrazine 24.2g (0.05 mol) of intermediate compound 2 were dissolved hot in 350 ml of propanol, and 28.5 g of p-toluenesulphonic acid were then added. 7.5 g (0.06 mol) of amyl nitrite were added to the resulting solution at 30°C and the reaction mixture was then stirred for 1 hour. The excess nitrate was destroyed by the addition of urea and reaction mixture was then introduced portionwise into a solution of 26 g of tin-II-chloride in 30 ml of concentrated hydrochloric acid at 0–5°C with vigorous stirring. The resulting precipitate is suction filtered, stirred up in 20% hydrochloric acid and again suction filtered. The crude product was then dissolved in ethyl acetate and treated with 30% sodium hydroxide solution. The solution in ethyl acetate was separated off and washed with water, and the solvent was evaporated. The residue was recrystallized from methanol. Yield: 19 g (M.p. 90°–93°C.)

d. Intermediate compound 4: β-(2-Methoxy-5-N,N-diethylsulphaminyl-anilino)-β-imino-propionic acid ethyl ester hydrochloride 5.16 g (0.02 mol) of 2-amino-anisole-sulfonic acid-4-diethylamide and 5.4 g (0.02 mol) of β-phenoxy-β-iminopropionic acid ethyl ester hydrochloride (for method of preparation see British patent application Ser. No. 00456/74 which is described below) in 20 ml of ethyl acetate were stirred together for 60 minutes at boiling point. When the reaction mixture was cold, 50 ml of petroleum ether were added and the product was suction filtered. Yield: 7.8 g.

e. Coupler No. 24

4.5 g (0.011 mol) of intermediate compound 4 and 5 g (0.01 mol) of intermediate compound 3 in 25 ml of methanol and 0.5 ml of glacial acetic acid were boiled on a water bath for 5 hours. When the reaction mixture was cold, the precipitate formed was suction filtered. The amidrazone intermediate product obtained in this way was stirred up in a solution of 0.3 of sodium in 50 ml of methanol for 90 minutes at room temperature to close the coupler ring.

The undissolved product was filtered off and the filtrate was neutralized with glacial acetic acid. 3 g of coupler 24 were obtained after recrystallization of the precipitate. M.p. 122°–124°C. Preparation of β-phenoxy-β-iminopropionic acid ethyl ester hydrochloride mentioned above is carried out as follows: mixture 94 g (1 mol) of phenol were dissolved in 113 g (1 mol) of ethyl cyanoacetate. 35.5 g (1 mol) of hydrogen chloride gas were introduced into this solution at −20°C with stirring. The temperature of the reaction mixture was raised to room temperature of the reaction mixture was raised to room temperature in the course of 3 hours while a slow stream of hydrogen chloride continued to be passed through. The reaction product solidified in the course of 2 days standing at room temperature. It was stirred up with ether, suction-filtered, washed with petroleum ether and dried in a desiccator. Yield: 180 g 74 % of the theory.

The couplers according to the invention are eminently suitable for use in light-sensitive silver halide emulsion layers of singlelayered or multilayered color photographic materials. The color couplers need not necessarily be incorporated in the light-sensitive layers but may be incorporated in a layer of binder adjacent to a light-sensitive silver halide emulsion layer.

The pyrazolone couplers according to the invention may be incorporated in photographic silver halide emulsions without having a deleterious effect on them. They are compatible with the hyrophilic photographic colloid layer in which they may be incorporated in the form of a finely divided dispersion in a solvent or directly dispersed in them and they cannot diffuse in these layers. When a color photographic material according to the invention is developed, the color couplers have excellent stability in the baths used for development. Furthermoe, the color couplers used according to the invention do not cause any unwanted discoloration in non-image areas.

The incorporation of the diffusion-fast couplers according to the invention in photographic emulsions or in a binder mixture may be carried out by any of the known methods. Water-soluble color couplers, for example those which contain one or more sulfo or carboxyl groups, may be added to the casting solutions from aqueous solution, optionally in the presence of alkali. Color couplers which are insoluble or only sparingly soluble in water are dissolved in a suitable high boiling or low boiling organic solvent or solvent mixture which may be miscible or immiscible with water, and the resulting solution, optionally in the presence of a wetting or dispersing agent, is dissolved in a hydrophilic colloid mixture which constitutes all or part of the binder in the colloid layer. The hydrophilic colloid mixture may, of course, in addition also contain all the usual ingredients.

The light-sensitive emulsions used may be emulsions of silver halides such as silver chloride, silver bromide or mixtures thereof, which may have a small silver iodide content of up to 10 mol % in one of the usual hydrophilic binders such as protein, in particular gelatine, polyvinyl alcohol, polyvinyl pyrrolidone, a cellulose derivative such as a carboxyalkylcellulose, in particular carboxymethyl cellulose or a derivative of alginic acid.

The emulsions may also be chemically sensitized, e.g. by adding compounds which contain sulfur such as allylisothiocyanates, allylthiourea or sodium thiosulfate at the stage of chemical ripening. Reducing agents may also be used as chemical sensitizers, e.g. the tin compounds described in Belgian patent specification Nos. 493,464 and 568,687, or polyamines such as diethylenetriamine or tin compounds or polyamines such as diethylene triamine or aminoethanesulfinic acid derivatives, e.g. according to Belgian patent specification No. 547,323.

Noble metals such as gold, platinum, palladium, iridium, ruthenium or rhodium and compounds of such metals are also suitable chemical sensitizers. This method of chemical sensitization has been described in the article by R. Koslowsky, Z.Wiss.Phot. 46 65 - 72 (1951).

The emulsions may also be sensitized with polyalkylene oxide derivatives, e.g. with a polyethylene oxide having a molecular weight of between 1000 and 20,000 or with condensation products of alkylene oxides and aliphatic alcohols, glycols, or cyclic dehydration products of hexitols, with alkyl substituted phenols, aliphatic carboxylic acids, aliphatic amines, aliphatic diamines and amides. The condensation products have a molecular weight of at least 700, preferably more than 1000. These sensitizers may, of course, be combined for the purpose of achieving special effects, as described in Belgian Pat. No. 537,278 and British patent specification No. 727,982.

The emulsions which contain color couplers may also contain spectral sensitizer, e.g. the usual mono- or polymethine dyes, such as cyanines, hemicyanies, streptocyanies, merocyaninesm oxonoles, hemioxonoles, styryl dyes or others, including trinuclear or higher nuclear methine dyes, for example rhodaycanines. Sensitizers of this kind have been described, for example, in the work By F.M.Hamer in "The Cyanine Dyes and Related Compounds" (1964), Interscience Publishers John Wiley & Sons.

The emulsions may contain the usual sentisizers, e.g. homopolar or salt-type compounds of mercury which contain aromatic or heterocyclic rings, such as mercapto-triazoles, simple mercury salts, sulfenium mercury double salts and other mercury compounds. Azaindenes are also suitable stabilizers, particularly tetra- or penta-azaindenes and especially those which are substituted with hydroxyl or amino groups. Compounds of this kind have been described in the article by Birr. Z.Wiss. Phot. 47 2 - 58 (1958). Other suitable stabilisers are inter alia heterocyclic mercapto compounds, e.g. phenylmercaptotetrazole, quaternary benzothiazole derivatives and benzotriazole.

The emulsions may be hardened in the usual manner, for example with formaldehyde or halogenated aldehydes which contain a carboxy group, such as mucobromic acid, diketones, methanesulfonic acid esters and dialdehydes.

The usual color developers are used for producing the dyes, e.g. the usual aromatic compounds based on phenylenediamine which contain at least one primary amino group. The following are examples of suitable color developers: N,N-Dimethyl-p-phenylene diamine, N,N-diethyl-p-phenylene diamine, monomethyl-p-phenylene diamine, 2-amino-5-diethylaminotoluene, N-butyl-N-β-sulfotobutyl-p-phenylene-diamine and 2-amino-5-(N-ethyl-N-β-methanesulonamidoethylamino)-toluene. Other suitable color developers have been described, for example, in J.Amer.Chem. Soc. 73 3000 to 3025 (1951).

The advantageous properties of the couplers according to the invention will be illustrated by the following Examples.

EXAMPLE 1

The following Example demonstrates that the couplers according to the invention are distinctly superior in their stability to light compared to similar couplers which contain resorcinol or pyrocatechol diether groups.

1. 2.87 g of couplers No. 5 are dissolved in 10 ml of ethyl acetate and emulsified in 50 ml of a 5% gelatine solution in which 0.4 g of sodium dodecylbenzenesulfonate had been dissolved as emulsifier.

The emulsion is then added to a silver halide emulsion which had a silver halide content of 0.024 mol, based on the quantity of coupler used (0.004 mol of coupler No.5) and the silver halide emulsion is cast on a transparent support layer of cellulose triacetate.

The photographic material prepared in this way is exposed behind a grey wedge, developed with a color developer and bleached and fixed in the usual manner.

| Color developer: | | |
| --- | --- | --- |
| Benzyl alcohol | 3.5 | cc |
| Sodium metaphosphate | 2 | g |
| Sodium sulfite sicc | 2 | g |
| 4-Amino-N-ethyl-(β-methane-sulfon-amidoethyl)-m-toluidine-sesquisulfate monohydrate | | |
| Sodium carbonate monohydrate | 50 | g |
| Potassium bromide | 2 | g |
| Water up to | 1 | l |
| pH = 10.75 ± 0.03 | | |

Color wedges which contain the following couplers instead of 2.87 g of coupler No. 5 are prepared in a similar manner:

2. 2.87 g of coupler A of the following formula

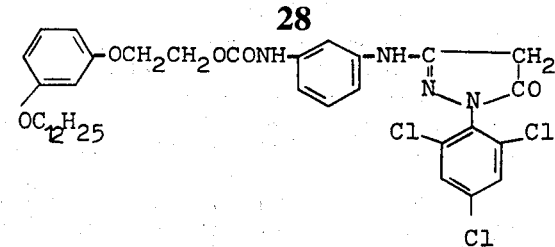

3. 2.87 g of coupler B of the following formula

Couplers A and B are comparative couplers containing resorcinol and pyrocatechol diether groups, respectively.

The magenta colored step wedges obtained were measured in an Ansco Densitometer. Each sample was divided into 2 parts and one part was tested for its stability to light by exposing it to $6 \times 10^6$ Lux hours in a box equipped with fluorescent tubes while the other part was exposed to $2.4 \times 10^6$ Lux hours with a Xenon lamp.

Table 2 below shows the percentage decrease in color density of the exposed step wedges compared with unexposed step wedges having an average color density of 1.5.

Table 2

| Photograhic material containing color coupler | Reduction after exposure to Xenon lamp | Reduction after exposure in illumination box |
| --- | --- | --- |
| 5 | − 24% | − 24% |
| A | − 43% | − 64% |
| B | − 42% | − 66% |

EXAMPLE 2

Emulsions which are prepared and processed as described in Example 1, except that 2.87 g of coupler 6, 8, 9 or 17 has been used instead of coupler No. 5, are measured behind an Ansco Densitometer as described in Example 1.

Other samples are prepared for comparison which are analogous except that instead of the couplers according to the invention, comparison couplers known in the art which do not contain a stabilizing hydroquinone diether group are used.

Coupler C

Coupler D

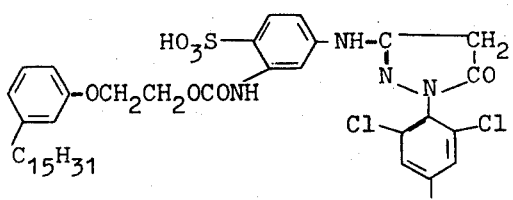

Coupler E

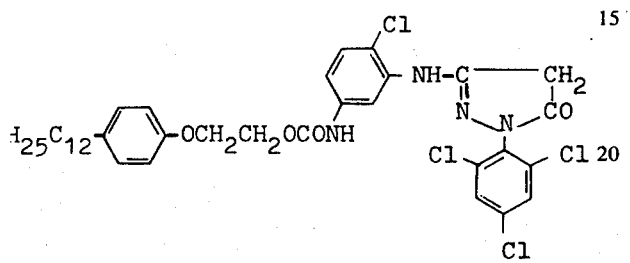

Coupler F

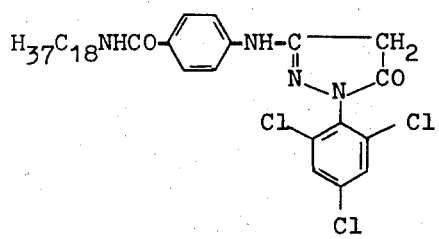

Comparison couplers C,D,E and F according to Russian Pat. No. 141,485 and British patent specification No. 956,261 are chosen to be as similar as possible to the couplers according to the invention.

The table below shows that the color couplers according to the invention are distinctly superior in their stability to light compared with the comparison couplers.

Table 3

| Photographic material containing color coupler | Reduction after exposure in Xenon lamp | Reduction after exposure in illumination box |
| --- | --- | --- |
| 6 | − 30% | − 30% |
| C | − 46% | − 52% |
| 8 | − 18% | − 10% |
| D | − 41% | − 47% |
| 9 | − 22% | − 26% |
| E | − 39% | − 40% |
| 17 | − 26% | − 28% |
| F | − 39% | − 65% |

We claim:

1. A light-sensitive color-photographic material which contains at least one silver halide emulsion layer and a pyrazolone coupler, characterized by having a 5-pyrazolone coupler group to which is attached in the 1- or 3- position of the 5-pyrazolone coupler in a substituent of the pyrazolone coupler in its 1- or 3-position or as a substituent of the pyrazolone coupler in its 3-position a hydroquinone diether group of the formula:

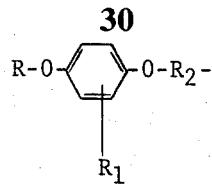

in which
$R_2$ represents an alkylene group, in which alkylene group one hydrogen may be substituted by an alkyl group and in cases where $R_2$ is attached to the 3-position or to one of the substituents in the 1- or 3-position of the pyrazolone coupler through a connecting member —OCONH—, the number of carbon atoms in the alkylene group is even,
R represents an alkyl or cycloalkyl group and
$R_1$ represents hydrogen or an alkyl group and wherein the substituents of the pyrazolone coupler in its 3-position are selected from the group consisting of alkyl, alkylamino, arylamino and acylamino and in its 1-position are selected from the group consisting of aryl and methyl substituted with carbamyl, phenyl or trifluoromethyl
and said pyrazolone coupler contains in its 3-position at least one of said 3-position substituents when the hydroquinone diether group is attached to the 1-position,
and said pyrazolone coupler contains in its 1-position at least one of said 1-position substituents when the hydroquinone diether group is attached to the 3-position.

2. A material as claimed in claim 1 in which the hydroquinone diether group is connected to the substituents in 1- or 3-position through a chemical bond or through a bivalent connecting member selected from the group consisting of —O—; —CONH—; —NHCO—; —NHCONH—; —COO— and —OCONH—, or is connected to the 3-position directly through a bivalent connecting member of said connecting member group.

3. A material as claimed in claim 1 in which $R_2$ represents an alkylene group which contains from 1 to 22 carbon atoms.

4. A material as claimed in claim 3 in which $R_2$ represents a methylene, ethylene, propylene or butylene group.

5. A material as claimed in claim 1 in which $R_2$ represents an alkylene group in which one hydrogen atom has been substituted by an alkyl group which contains 1 to 18 carbon atoms.

6. A material as claimed in claim 1 in which $R_2$ represents an alkylene group in which the hydrogen atom which is substituted by an alkyl group in the α-position to the ether oxygen.

7. A material as claimed in claim 1 in which R represents an alkyl group containing from 1 to 18 carbon atoms or a cyclohexyl or cyclopentyl group.

8. A material as claimed in claim 1 in which $R_1$ represents an alkyl group which contains from 1 to 14 carbon atoms.

9. A material as claimed in claim 8 in which $R_1$ represents an alkyl group which contains from 4 to 14 carbon atoms.

10. A material as claimed in claim 1 in which the 5-pyrazolone coupler is a 1-phenyl pyrazolone coupler which contains in its phenyl group at least one chlorine atom.

* * * * *